US008598149B2

(12) United States Patent
Belanoff (10) Patent No.: US 8,598,149 B2
(45) Date of Patent: Dec. 3, 2013

(54) OPTIMIZING MIFEPRISTONE LEVELS IN PLASMA SERUM OF PATIENTS SUFFERING FROM MENTAL DISORDERS TREATABLE WITH GLUCOCORTICOID RECEPTOR ANTAGONISTS

(75) Inventor: Joseph K. Belanoff, Woodside, CA (US)

(73) Assignee: Corcept Therapeutics, Inc., Menlo Park, CA (US)

( * ) Notice: Subject to any disclaimer, the term of this patent is extended or adjusted under 35 U.S.C. 154(b) by 866 days.

(21) Appl. No.: 12/199,114

(22) Filed: Aug. 27, 2008

(65) Prior Publication Data

US 2009/0062248 A1 Mar. 5, 2009

Related U.S. Application Data

(60) Provisional application No. 60/969,027, filed on Aug. 30, 2007.

(51) Int. Cl.
*A61K 31/56* (2006.01)
(52) U.S. Cl.
USPC .......................................... 514/178; 514/182

(58) Field of Classification Search
USPC ................................................. 514/182, 178
See application file for complete search history.

(56) References Cited

U.S. PATENT DOCUMENTS 6,964,953 B2 * 11/2005 Belanoff ..................... 514/178

OTHER PUBLICATIONS

Sarkar, European Journal of Obstetrics and Gynecology and Reproductive Biology, 2002;101:113-120.*
Medical Encyclopedia of Medline (http:// http://www.nlm.nih.gov/medlineplus/ency/article/003430.htm, Oct. 2005.*

* cited by examiner

*Primary Examiner* — San-Ming Hui
(74) *Attorney, Agent, or Firm* — Kilpatrick Townsend & Stockton LLP.

(57) ABSTRACT

The present invention provides a method for optimizing levels of mifepristone in a patient suffering from a mental disorder amenable to treatment by mifepristone. The method comprises the steps of treating the patient with seven or more daily doses of mifepristone over a period of seven or more days; testing the serum levels of the patient to determine whether the blood levels of mifepristone are greater than 1300 ng/mL; and adjusting the daily dose of the patient to achieve mifepristone blood levels greater than 1300 ng/mL.

7 Claims, 6 Drawing Sheets

OPTIMIZING MIFEPRISTONE LEVELS IN PLASMA SERUM OF PATIENTS SUFFERING FROM MENTAL DISORDERS TREATABLE WITH GLUCOCORTICOID RECEPTOR ANTAGONISTS

CROSS-REFERENCES TO RELATED APPLICATIONS

This application claims priority to U.S. Provisional Application No. 60/969,027, filed Aug. 30, 2007, the disclosure of which is incorporated herein in its entirety.

STATEMENT AS TO RIGHTS TO INVENTIONS MADE UNDER FEDERALLY SPONSORED RESEARCH AND DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK

NOT APPLICABLE

BACKGROUND OF THE INVENTION

It has been surprisingly discovered that administration of the same dose of mifepristone can produce widely varying blood serum levels in different patients. The varied blood serum levels can result in some patients not receiving an efficacious dose of mifepristone. For the same dose of mifepristone, the blood serum levels can differ by as much as 800% from one patient to another. Thus, a method for ensuring that the blood serum levels of mifepristone remain in an efficacious and safe range is needed.

BRIEF SUMMARY OF THE INVENTION

In one embodiment, the present invention provides a method for optimizing levels of mifepristone in a patient suffering from a mental disorder amenable to treatment by mifepristone, the method comprising: treating the patient with seven or more daily doses of mifepristone over a period of seven or more days; testing the serum levels of the patient to determine whether the blood levels of mifepristone are greater than 1300 ng/mL; and adjusting the daily dose of the patient to achieve mifepristone blood levels greater than 1300 ng/mL.

In some embodiments, the mental disorder is a member selected from the group consisting of a stress disorder, delirium, mild cognitive impairment (MCI), dementia, psychosis and psychotic major depression. In other embodiments, the stress disorder is a member selected from the group consisting of Acute Stress Disorder, Post-Traumatic Stress Disorder and Brief Psychotic Disorder with Marked Stressor(s).

In another embodiment, each of the seven or more daily doses of mifepristone are administered orally. In other embodiments, the patient is treated with 28 or more daily doses over a period of 28 or more days.

In a further embodiment, the testing is performed by a plasma sampling collection device suitable for detecting mifepristone serum levels.

In other embodiments, the adjusting step comprises increasing the daily dose of the patient to achieve mifepristone blood levels greater than 1300 ng/mL.

In a second embodiment, the present invention provides a kit for treating a mental disorder amenable to treatment by mifepristone, the kit comprising: seven daily doses of mifepristone; and a plasma sampling collection device suitable for detecting mifepristone serum levels.

DETAILED DESCRIPTION OF THE INVENTION

I. Introduction

Figure 1:
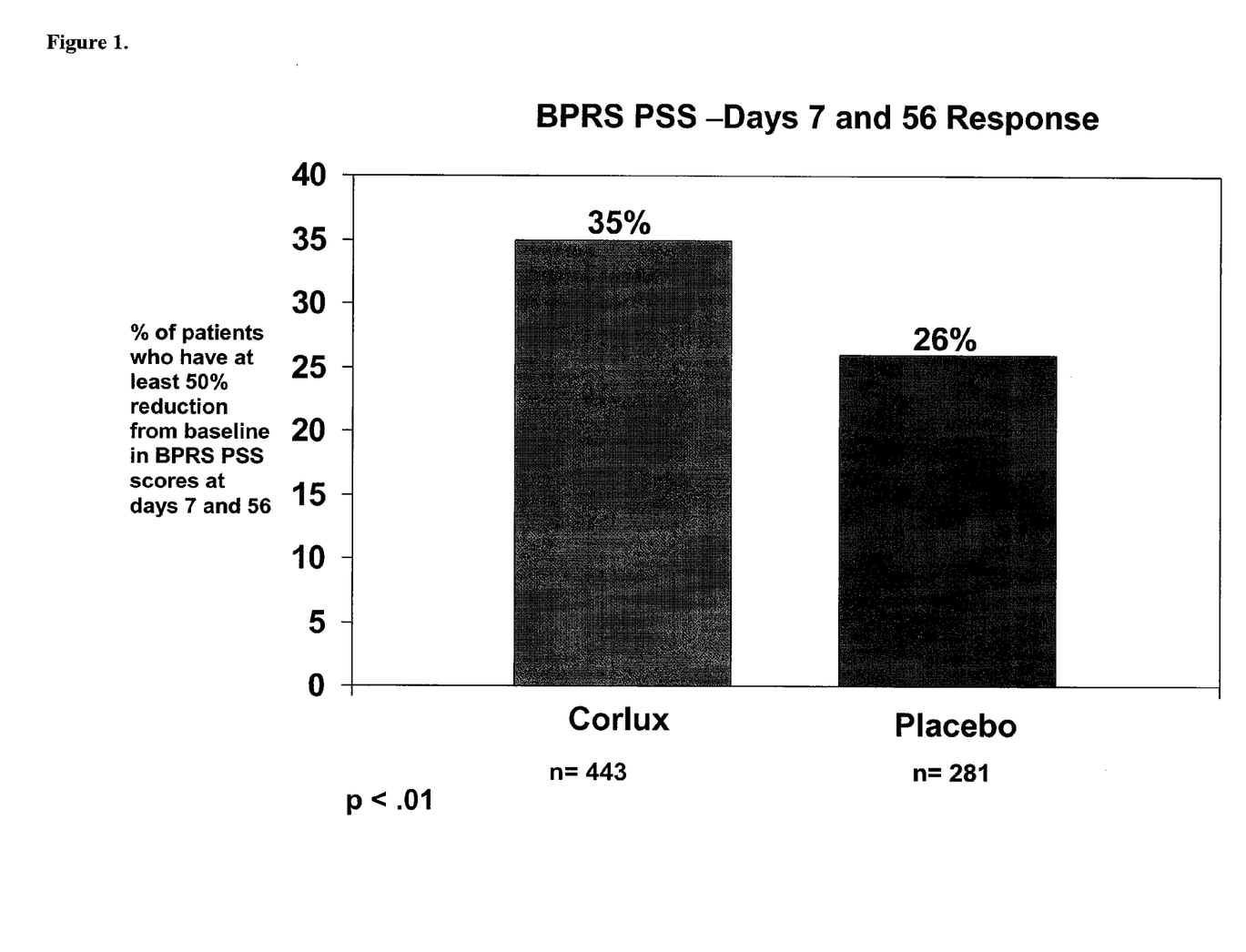
FIG. 1 shows a comparison of patients receiving Corlux vs. placebo on primary endpoint (OC) for all studies. Of the patients receiving Corlux, 35% of the patients showed at least a 50% reduction from baseline in BPRS PSS scores at days 7 and 56, versus 26% of patients receiving the placebo.
Figure 2:
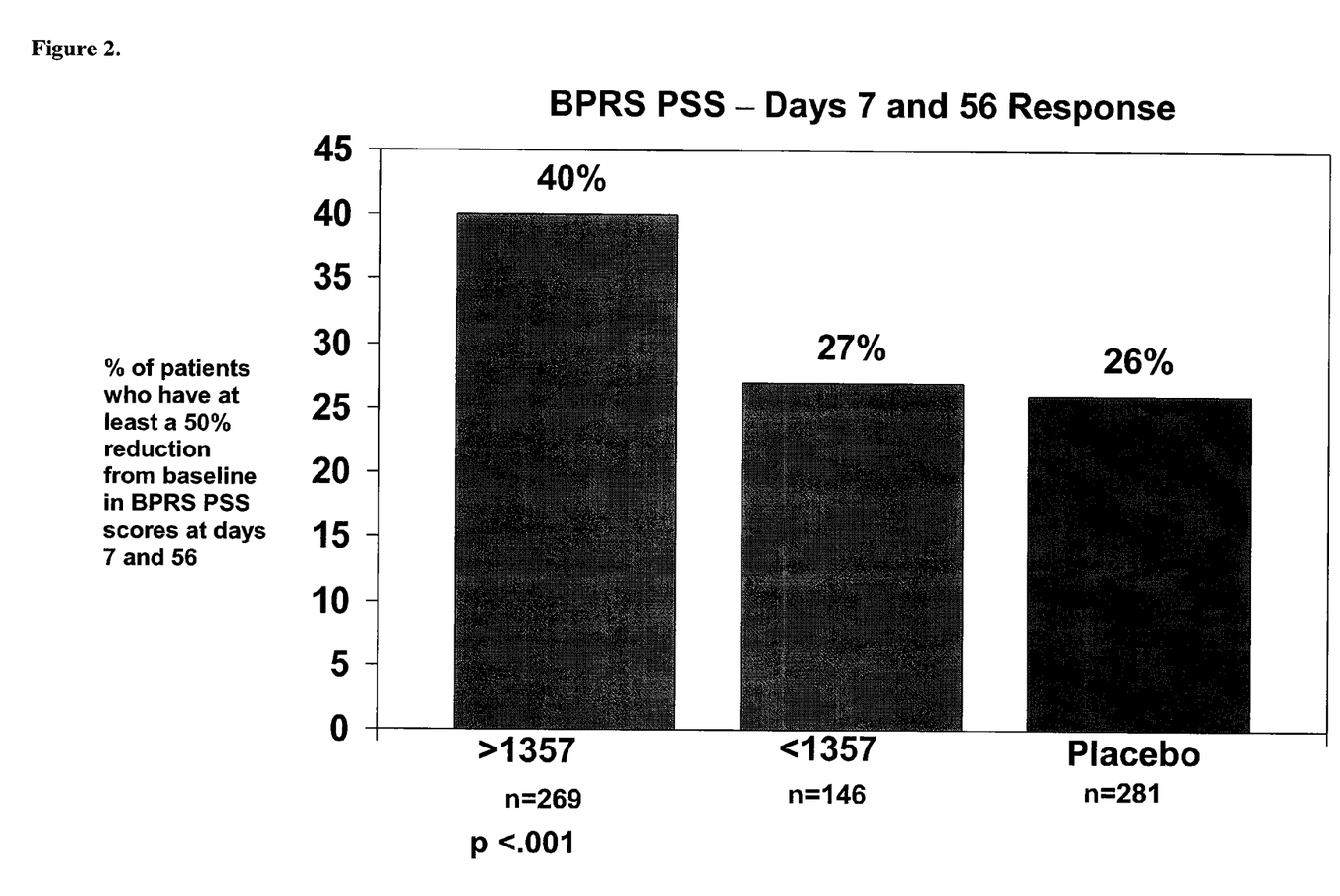
FIG. 2 shows a comparison of patients with plasma levels>1357 ng/mL vs.<1357 ng/mL vs. placebo (OC) for all studies. Of the patients having plasma levels of greater than 1357 ng/mL, 40% of the patients showed at least a 50% reduction from baseline in BPRS PSS scores at days 7 and 56, versus 27% of patients having plasma levels of less than 1357 ng/mL and 26% of patients receiving the placebo.
Figure 3:
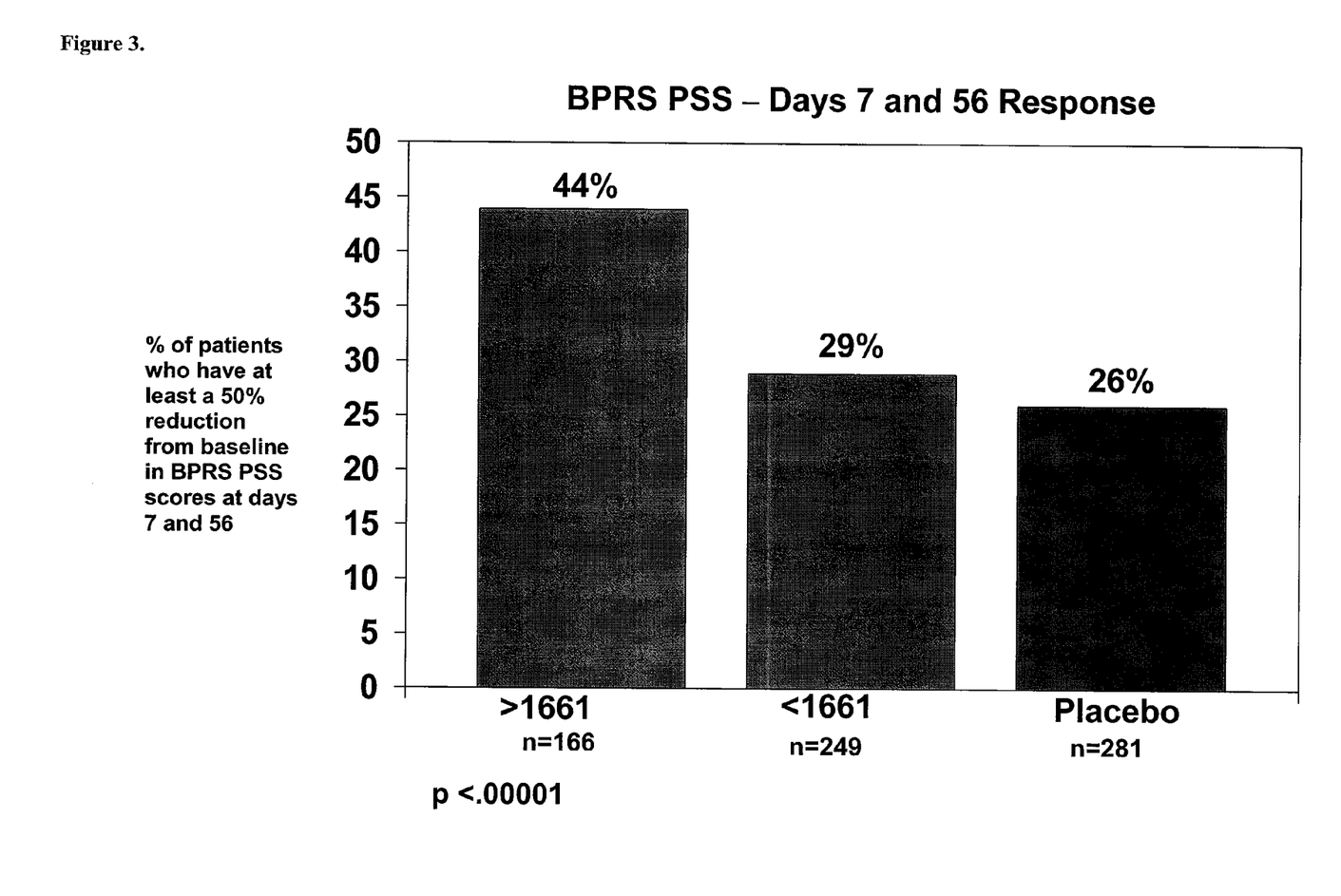
FIG. 3 shows a comparison of patients with plasma levels>1661 ng/ml vs. placebo (OC) for all studies. Of the patients having plasma levels of greater than 1661 ng/mL, 44% of the patients showed at least a 50% reduction from baseline in BPRS PSS scores at days 7 and 56, versus 29% of patients having plasma levels of less than 1661 ng/mL and 26% of patients receiving the placebo.
Figure 4:
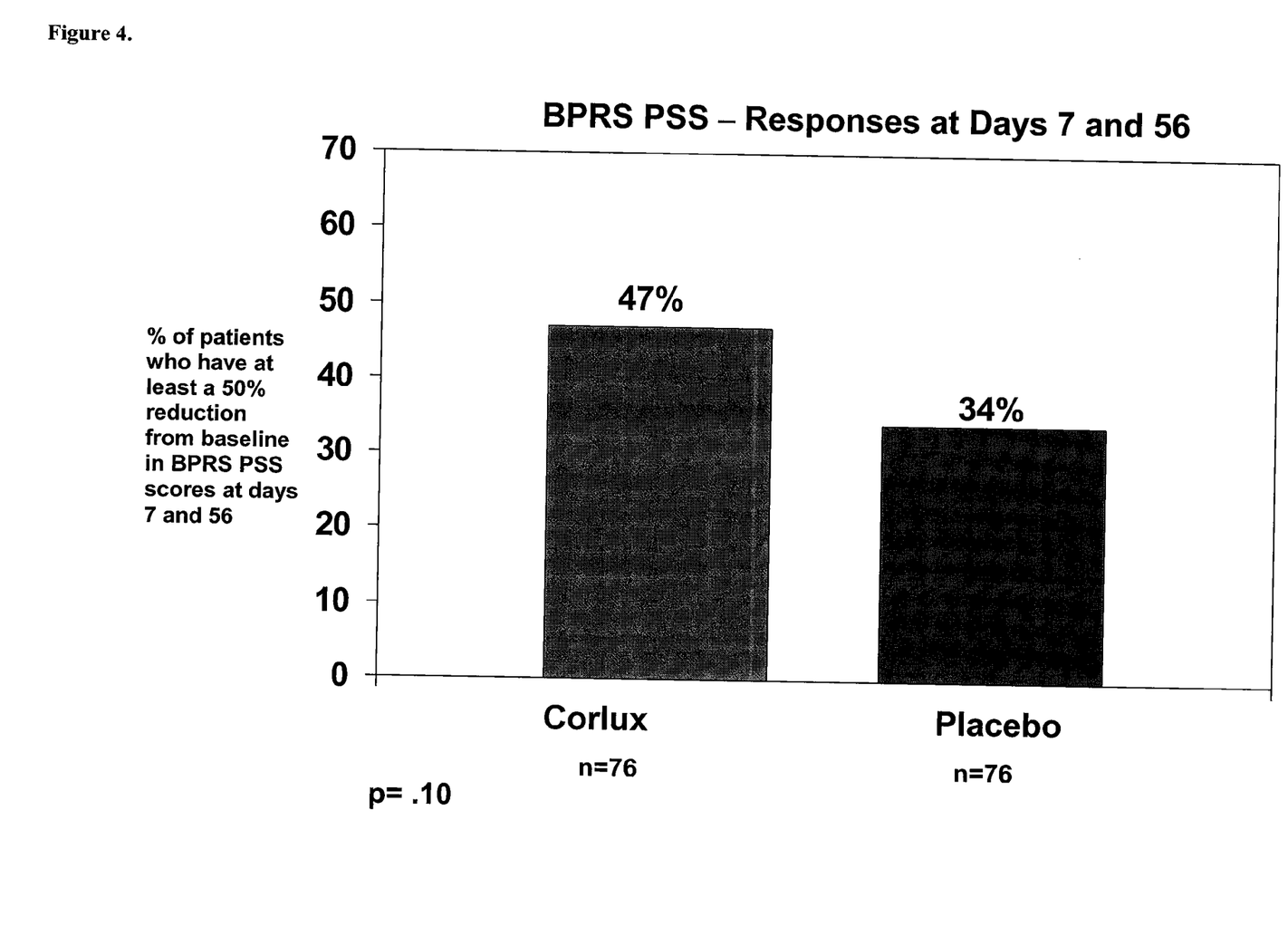
FIG. 4 shows a comparison of patients receiving Corlux vs. placebo on primary endpoint (OC) for the 1200 mg group. Of the patients receiving the 1200 mg dose of Corlux, 47% of the patients showed at least a 50% reduction from baseline in BPRS PSS scores at days 7 and 56, versus 34% of patients receiving the placebo.
Figure 5:
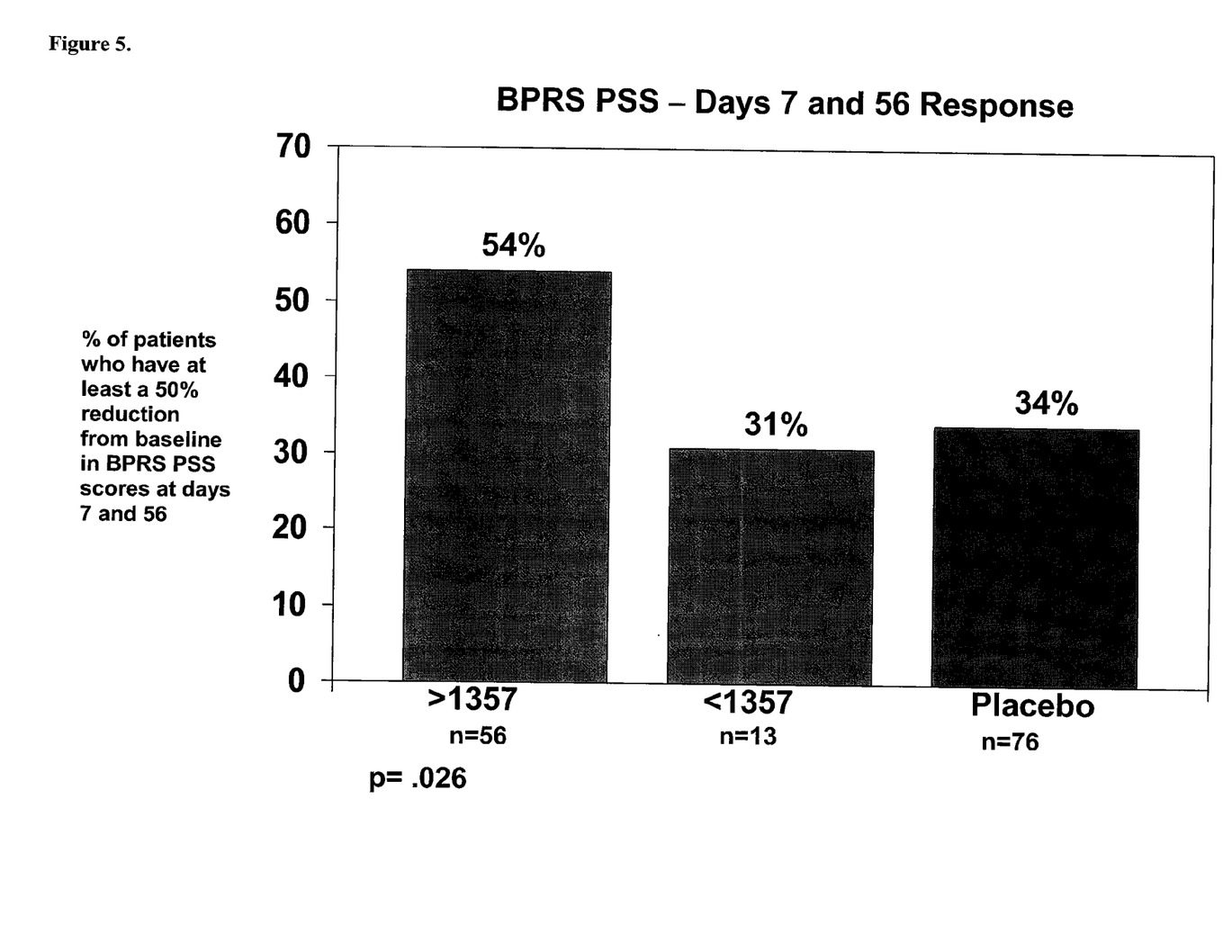
FIG. 5 shows a comparison of patients with plasma levels>1357 ng/ml vs. placebo (OC) for the 1200 mg group. Of the patients in the 1200 mg group having plasma levels of greater than 1357 ng/mL, 54% of the patients showed at least a 50% reduction from baseline in BPRS PSS scores at days 7 and 56, versus 31% of patients having plasma levels of less than 1357 ng/mL and 34% of patients receiving the placebo.
Figure 6:
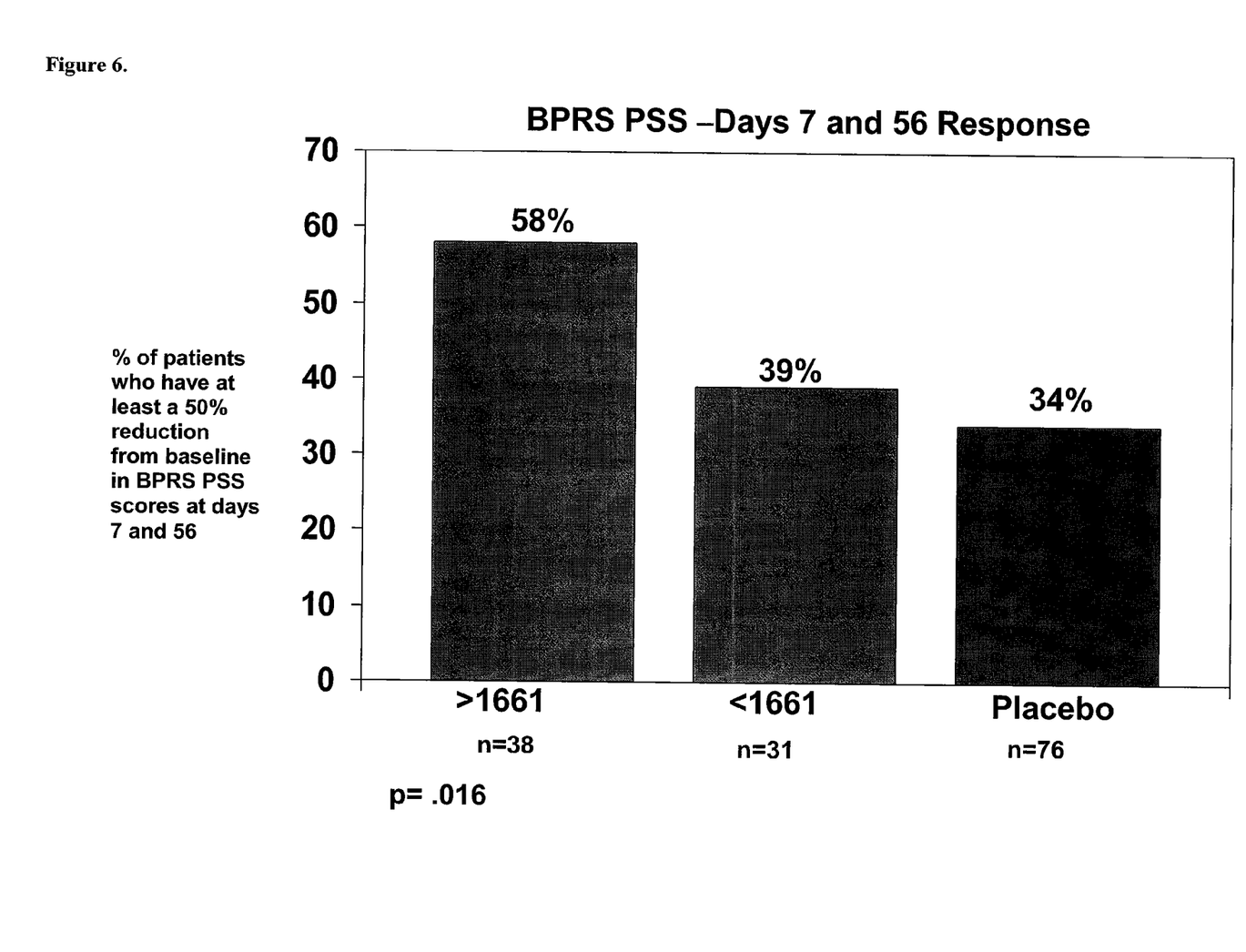
FIG. 6 shows a comparison of patients with plasma levels>1661 ng/ml vs. placebo (OC) for the 1200 mg group. Of the patients in the 1200 mg group having plasma levels of greater than 1661 ng/mL, 58% of the patients showed at least a 50% reduction from baseline in BPRS PSS scores at days 7 and 56, versus 39% of patients having plasma levels of less than 1661 ng/mL and 34% of patients receiving the placebo.

Administration of the same dose of mifepristone can produce widely varying mifepristone blood serum levels in different patients. For the same dose, the blood serum levels can differ by as much as 800% from one patient to another. For those patients with lower blood serum levels, the effectiveness of mifepristone treatment can suffer significantly. The present invention provides a method for optimizing the blood serum levels of mifepristone so that the blood serum levels remain in an efficacious range and the patient receives the necessary treatment.

The method of the present invention optimizes blood serum levels of mifepristone in a patient suffering from a mental disorder amenable to treatment by mifepristone by first treating the patient with mifepristone. The treatment can be for any appropriate period of time, such as seven or more daily doses over a period of seven or more days. Following treatment for an appropriate period of time, the serum levels of the patient are tested to determine whether the blood levels of mifepristone are greater than 1300 ng/mL. The daily dose of the patient is then adjusted in order to achieve mifepristone blood levels of greater than 1300 ng/mL.

II. Definitions

The term "amenable to treatment by mifepristone" refers to a condition that is known to be treated by glucocorticoid antagonists such as mifepristone. Conditions such as mental disorders (discussed below) are amenable to treatment by mifepristone.

The term "mental disorder" refers to disorders of the mind that can be treated with a glucocorticoid antagonist such as mifepristone. Mental disorders amenable to treatment by the methods of the present invention include, but are not limited to, a stress disorder, delirium, mild cognitive impairment (MCI), dementia, psychosis and psychotic major depression.

The term "stress disorder" refers to a psychiatric condition precipitated by exposure to a traumatic or stressful event. Stress disorders include Acute Stress Disorder, Post-Traumatic Stress Disorder, and Brief Psychotic Disorder with Marked Stressor(s).

The term "Acute Stress Disorder" refers to a psychiatric condition in its broadest sense, as defined in American Psychiatric Association: Diagnostic and Statistical Manual of Mental Disorders, Fourth Edition, Text Revision, Washington, D.C., 2000 ("DSM-IV-TR"). The DSM-IV-TR defines "Acute Stress Disorder" as characterized by anxiety, dissociative, and other symptoms occurring within 1 month after exposure to an extreme traumatic stressor. The DSM-IV-TR sets forth a generally accepted standard for diagnosing and categorizing Acute Stress Disorder.

The term "Brief Psychotic Disorder with Marked Stressor(s)" refers to a psychiatric condition in its broadest sense, as defined in DSM-IV-TR. The DSM-IV-TR defines "Brief Psychotic Disorder with Marked Stressor(s)" as a sudden but brief onset of psychotic symptoms developing shortly after and apparently in response to one or more stressful events. The DSM-IV-TR sets forth a generally accepted standard for diagnosing and categorizing Brief Psychotic Disorder with Marked Stressor(s).

The term "delirium" refers to a psychiatric condition in its broadest sense, as defined in American Psychiatric Association: Diagnostic and Statistical Manual of Mental Disorders, Fourth Edition, Text Revision, Washington, D.C., 2000 ("DSM-IV-TR"). The DSM-IV-TR defines "delirium" as a disturbance of consciousness, developing over a short period of time, accompanied by a change in cognition that cannot be better accounted for by a preexisting or evolving dementia. The DSM-IV-TR sets forth a generally accepted standard for diagnosing and categorizing delirium.

The term "dementia" refers to a psychiatric condition in its broadest sense, as defined in American Psychiatric Association: Diagnostic and Statistical Manual of Mental Disorders, Fourth Edition, Washington, D.C., 1994 ("DSM-IV"). The DSM-IV defines "dementia" as characterized by multiple cognitive deficits that include impairments in memory and lists various dementias according to presumed etiology. The DSM-IV sets forth a generally accepted standard for such diagnosing, categorizing and treating of dementia and associated psychiatric disorders.

The term "mild cognitive impairment (MCI)" refers to a category of memory and cognitive impairment that is typically characterized by a clinical dementia rating (CDR) of 0.5 (see, e.g., Hughes et al., *Brit. J. Psychiat.* 140:566-572, 1982) and further characterized by memory impairment, but not impaired function in other cognitive domains. Memory impairment is preferably measured using tests such as a "paragraph test". A patient diagnosed with MCI often exhibits impaired delayed recall performance. MCI is typically associated with aging and generally occurs in patients who are 45 years of age or older.

The term "mifepristone" refers to a family of compositions also referred to as RU486, or RU38.486, or 17-beta-hydroxy-11-beta-(4-dimethyl-aminophenyl)-17-alpha-(1-propynyl)-estra-4,9-dien-3-one), or 11-beta-(4-dimethylaminophenyl)-17-beta-hydroxy-17-alpha-(1-propynyl)-estra-4,9-dien-3-one), or analogs thereof, which bind to the glucocorticoid receptor (GR), typically with high affinity, and inhibit the biological effects initiated/mediated by the binding of any cortisol or cortisol analogue to a GR receptor (as discussed within). Salts, hydrates and prodrugs of mifepristone are all within the scope of the present invention.

The term "Post-Traumatic Stress Disorder" refers to a psychiatric condition in its broadest sense, as defined in DSM-IV-TR. The DSM-IV-TR defines "Post-Traumatic Stress Disorder" as characterized by persistent re-experiencing of an extreme traumatic event. The DSM-IV-TR sets forth a generally accepted standard for diagnosing and categorizing Post-Traumatic Stress Disorder.

The term "psychotic" as used herein refers to a psychiatric condition in its broadest sense, as defined in the DSM-IV (Kaplan, ed. (1995) supra) and described below. The term "psychotic" has historically received a number of different definitions, ranging from narrow to broadly described. A psychotic condition can include delusions or prominent hallucinations, including prominent hallucinations that the individual realizes are hallucinatory experiences, and those with hallucinations occurring in the absence of insight into their pathological nature. Finally, the term includes a psychotic condition characterized by a loss of ego boundaries or a gross impairment in reality testing. Unlike this definition, which is broad and based primarily on symptoms, characterization of psychosis in earlier classifications (e.g., DSM-II and ICD-9) were more inclusive and focused on the severity of functional impairment (so that a mental disorder was termed "psychotic" if it resulted in "impairment" that grossly interferes with the capacity to meet ordinary demands of life). Different disorders which have a psychotic component comprise different aspects of this definition of "psychotic." For example, in schizophreniform disorder, schizoaffective disorder and brief psychotic disorder, the term "psychotic" refers to delusions, any prominent hallucinations, disorganized speech, or disorganized or catatonic behavior. In psychotic disorder due to a general medical condition and in substance-induced psychotic disorder, "psychotic" refers to delusions or only those hallucinations that are not accompanied by insight. Finally, in delusional disorder and shared psychotic disorder, "psychotic" is equivalent to "delusional" (see DSM-IV, supra, page 273).

Objective tests can be also be used to determine whether an individual is psychotic and to measure and assess the success of a particular treatment schedule or regimen. For example, measuring changes in cognitive ability aids in the diagnosis and treatment assessment of the psychotic patient. Any test known in the art can be used, such as the so-called "Wallach Test," which assesses recognition memory (see below, Wallach (1980) J. Gerontol. 35:371-375). Another example of an objective text which can be used to determine whether an individual is psychotic and to measure efficacy of an antipsychotic treatment is the Stroop Color and Word Test ("Stroop Test") (see Golden, C. J., Cat. No. 30150M, In A Manual for Clinical and Experimental Uses, Stoelting, Wood Dale, Ill.) The Stroop Test is an objective neuropsychiatric test that can differentiate between individuals with psychosis and those without, and is described in detail below.

The term "psychosis" refers to a psychiatric symptom, condition or syndrome in its broadest sense, as defined in the DSM-IV (Kaplan, ed. (1995) supra), comprising a "psychotic" component, as broadly defined above. The term psychosis can refer to a symptom associated with a general medical condition, a disease state or other condition, such as a side effect of drug abuse (a substance-induced disorder) or as a side effect of a medication. Alternatively, the term psychosis can refer to a condition or syndrome not associated with any disease state, medical condition, drug intake or the like.

Psychosis is typically defined as a mental disorder or condition causing gross distortion or disorganization of a person's mental capacity, affective response, and capacity to recognize reality, communicate, and relate to others to the degree of interfering with his capacity to cope with the ordinary demands of everyday life.

The term "psychotic major depression," also referred to as "psychotic depression" (Schatzberg (1992) Am. J. Psychiatry 149:733-745), "psychotic (delusional) depression" (Ibid.), "delusional depression" (Glassman (1981) supra) and, "major depression with psychotic features" (see the DSM-III-R), refers to a distinct psychiatric disorder which includes both depressive and psychotic features. Individuals manifesting both depression and psychosis, i.e. psychotic depression, are herein referred to as "psychotic depressives." It has been long-recognized in the art as a distinct syndrome, as described, for example, by Schatzberg (1992) supra. Illustrative of this distinctness are studies which have found significant differences between patients with psychotic and nonpsychotic depression in glucocorticoid activity, dopamine-beta-hydroxylase activity, levels of dopamine and serotonin metabolites, sleep measures and ventricle to brain ratios. Psychotic depressives respond very differently to treatment compared to individuals with other forms of depression, such as "non-psychotic major depression." Psychotic depressives have a low placebo response rate and respond poorly to antidepressant therapy alone (without concurrent anti-psychotic treatment). Psychotic depressives are markedly unresponsive to tricyclic (anti-depressive) drug therapy (Glassman, et al. (1975) supra). While psychotic depressives can respond to electroconvulsive therapy (ECT), their response time is relatively slow and the ECT has a high level of related morbidity. Clinical manifestations and diagnostic parameters of "psychotic major depression" is described in detail in the DSM-IV (Kaplan, ed. (1995) supra). Thus, due to its unique pathophysiology, high rate of morbidity and response to treatment, there is great practical need to differentially diagnose and specifically treat psychotic major depression as compared to non-psychotic depression.

The term "optimizing" refers to the process of testing mifepristone blood levels and adjusting the dosage of mifepristone administered to the patient in need in order to achieve mifepristone blood levels above 1300 ng/mL.

The terms "treat", "treating" and "treatment" collectively refer to any indicia of success in the treatment or amelioration of an injury, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being; or, in some situations, preventing the onset of dementia. The treatment or amelioration of symptoms can be based on objective or subjective parameters; including the results of a physical examination, neuropsychiatric exams, and/or a psychiatric evaluation.

The term "testing" refers to determining the mifepristone blood levels in a patient. The testing can be performed by any suitable instrument, such as a plasma sampling collection device capable of detecting mifepristone serum levels.

III. Method for Optimizing Mifepristone Levels

Administration of the same dose of mifepristone to different patients can produce widely varying blood serum levels, varying by up to 800% from one patient to another, resulting in decreased efficacy. The present invention provides a method for optimizing the blood serum levels of mifepristone so that the blood serum levels remain in an efficacious range and the patient receives the necessary treatment.

A. Patients in Need

Patients amenable to treatment with mifepristone according to the method of the present invention suffer from any mental disorder. Exemplary mental disorders include, but are not limited to, a stress disorder, delirium, mild cognitive impairment (MCI), dementia, psychosis and psychotic major depression.

Stress disorders treatable by the methods of the present invention include, but are not limited to, Acute Stress Disorder (ASD), Post-Traumatic Stress Disorder and Brief Psychotic Disorder with Marked Stressor(s).

Acute Stress Disorder (ASD) is characterized by a constellation of symptoms, lasting at least two days, that appear and resolve within one month of exposure to an extreme traumatic stressor. If symptoms appear or persist beyond one month after exposure to the traumatic stressor, the patient may be considered to suffer from Post-Traumatic Stress Disorder rather than ASD. ASD is a common precursor to Post-Traumatic Stress Disorder, and up to 80% of trauma survivors initially suffering from ASD will meet the diagnostic criteria for Post-Traumatic Stress Disorder six months later (see Brewin et al., Am J Psychiatry 156:360-6, 1999).

Patients develop ASD following exposure to an extreme traumatic stressor (DSM-IV-TR Criterion A). A person must respond to the stressor with intense fear, helplessness, or horror to be diagnosed with ASD. ASD may develop from direct experience of traumatic events, including violent crimes, physical trauma, combat, diagnosis with a life-threatening illness, and natural or manmade disasters. Patients may also develop ASD from witnessing or learning about traumatic events that happen to others, especially family members or close friends. Unexpected exposure to death, dead bodies, or body parts may also induce ASD.

A diagnosis of ASD requires that the person meet several other symptomatic criteria. The person must experience three or more dissociative symptoms in connection with the traumatic stressor (Criterion B). Dissociative symptoms include a subjective sense of numbing or detachment, a reduction in awareness of surroundings, derealization, depersonalization, and dissociative amnesia. Furthermore, ASD requires that the victim persistently re-experience the traumatic event, though recurrent images, thoughts, dreams, illusions, flashbacks, sense of reliving the event, or distress upon exposure to reminders of the event (Criterion C). The person must display marked avoidance of stimuli that arouse recollection of the trauma (Criterion D) and marked symptoms of anxiety or increased arousal (Criterion E). Finally, in addition to the time requirements described above, a diagnosis of ASD requires that the disturbance cause significant distress; or life impairment, and not be due to another psychiatric or physiological condition (Criteria F-H).

Like Acute Stress Disorder, Post-Traumatic Stress Disorder (PTSD) emerges following exposure to an extreme traumatic stressor, and is characterized by persistent reexperiencing of the traumatic event, avoidance of stimuli associated with the trauma, and anxiety or increased arousal. The types of traumatic stressors giving rise to PTSD, and the manifestations of PTSD symptoms, are identical to those described above for ASD, but for three differences. First, the dissociative symptoms required for a diagnosis of ASD are not required for a diagnosis of PTSD, although dissociative symptoms may commonly be seen in PTSD patients. Secondly, PTSD need not arise within one month of exposure to the traumatic stressor, and may emerge months or years after the traumatic event. Thirdly, in contrast to the one month maximum duration of symptoms required for a diagnosis of ASD, symptoms must persist for at least one month in order for a diagnosis of PTSD to be made.

A Brief Psychotic Disorder is a short-term (between one day and one month) disturbance involving the sudden onset of at least one psychotic symptom, such as delusions, hallucinations, disorganized speech, or grossly disorganized or catatonic behavior. Brief Psychotic Disorders exclude those induced by a general medical condition. If psychotic symptoms develop shortly after, and apparently in response to, one or more severely stressful events, the disturbance is diagnosed as Brief Psychotic Disorder with Marked Stressor(s) (formerly labeled "brief reactive psychosis" in DSM-III-R). Brief Psychotic Disorder with Marked Stressor(s) is treatable by the glucocorticoid receptor antagonists of the present invention.

Delirium is characterized by disturbances of consciousness and changes in cognition that develop over a relatively short period of time. The disturbance in consciousness is often manifested by a reduced clarity of awareness of the environment. The patient displays reduced ability to focus, sustain or shift attention (DSM-IV-TR diagnostic Criterion A). Accompanying the disturbance in consciousness, delirium patients display a disturbance in cognition (e.g., memory impairment, disorientation, language difficulties) or perceptual disturbances (e.g., misinterpretations, illusions, or hallucinations) (Criterion B). To be considered delirium, these disturbances in consciousness, cognition, or perception should develop over a short period of time and tend to fluctuate during the course of the day (Criterion C).

Delirium may arise from a number of general medical conditions, including central nervous system disorders (e.g., trauma, stroke, encephalopathies), metabolic disorders (e.g., renal or hepatic insufficiency, fluid or electrolyte imbalances), cardiopulmonary disorders (e.g., congestive heart failure, myocardial infarction, shock), and systemic illnesses or effects (e.g., infections, sensory deprivation, and postoperative states). Glucocorticoid receptor antagonists are also effective to treat Substance-Induced Delirium (e.g., delirium induced by substance intoxication or withdrawal, medication side effects, and toxin exposure). Delirium may arise from multiple simultaneous etiologies (e.g., a combination of a general medical condition and substance intoxication) and such delirium, as well as delirium of unknown or unclassified origin, may be treated with the glucocorticoid receptor antagonists of the present invention.

Mild cognitive impairment (MCI) is characterized as a mild impairment of cognition categorized as a CDR of 0.5 that is associated with deficits in a memory task test, such as a paragraph test. An MCI patient is fully oriented, but demonstrates mild consistent forgetfulness. Impairment in cognitive domains other than memory, such as problem solving and judgment is doubtful, if present at all, and, further, the MCI patient does not demonstrate impairment in functioning in the community or at home. A patient with MCI scores normally on standard tests of dementia.

There are various means to diagnose the onset of MCI and to assess the efficacy of treatment using the methods of the invention. These include the administration of psychiatric tests to determine the CDR, the administration of memory tests, and the administration of psychiatric tests for dementia, which are used to exclude a diagnosis of dementia. The results of these test may be considered in conjunction with other objective physical tests as described below. These means are also useful for assessing the efficacy of the methods of the invention in improving memory or decreasing or diminishing further impairment in memory or cognitive decline in a patient with MCI. Subjective and objective criteria can be used to measure and assess the success of a particular GR antagonist, pharmaceutical formulation, dosage, treatment schedule or regimen. The features (symptoms) of and criteria for diagnosing MCI are described, e.g., in Petersen et al., Arch. Neurol. 56:303-308, 1999.

The dementia treated in the methods of the invention encompasses a broad range of mental conditions and symptoms, as broadly described in the DSM-IV. While the practitioner can use any set of prescribed or empirical criteria to diagnose the presence of dementia as an indication to practice the methods of the invention, some illustrative diagnostic guidelines and examples of relevant symptoms and conditions are described below.

The DSM-IV states that dementias typically associated with Alzheimer's disease (dementia of the Alzheimer's type), "vascular dementia" (also known as multi-infarct dementia), or "dementia due to general medical conditions," e.g., human immunodeficiency virus (HIV-1) disease, head trauma, Parkinson's disease, or Huntington's disease (further discussed, below). Dementias can also be "substance-induced persisting dementia," i.e., due to a drug of abuse, a medication, or toxin exposure, "dementia due to multiple etiologies," or a "dementia not otherwise specified" if the etiology is indeterminate.

Psychosis can be manifested as a mental illness in the form of a syndrome or as an element of a variety of disease processes. There are various means to diagnose these various forms of psychosis and assess the success of treatment. These means include classical psychological evaluations in addition to the various laboratory procedures described above. Such means are well-described in the scientific and patent literature, and some illustrative examples are provided below.

The psychosis ameliorated in the methods of the invention encompasses a broad range of mental conditions and symptoms, as broadly described in the DSM-IV (Kaplan, ed. (1995) supra). Psychosis can refer to a symptom associated with a general medical condition, a disease state or other condition, such as a side effect of drug abuse (a substance-induced disorder) or as a side effect of a medication. While the practitioner can use any set of proscribed or empirical criteria to diagnose the presence of a psychosis as an indication to practice the methods of the invention, some illustrative diagnostic guidelines and examples of relevant symptoms and conditions are described below.

Psychiatric conditions, such as psychosis, can be further diagnosed and evaluated using any of the many tests or criteria well-known and accepted in the fields of psychology or psychiatry.

The features (symptoms) of and criteria for diagnosing psychotic disorders, such as psychotic major depression, are further described DSM-IV, supra. While the practitioner can use any criteria or means to evaluate whether an individual is psychotic to practice the methods of the invention, the DSM-IV sets forth a generally accepted standard for such diagnosing, categorizing and treating of psychiatric disorders, including psychosis. Several illustrative examples of such criteria utilized in the methods of the invention are set forth below.

Psychosis is typically characterized as a mental disorder or condition causing gross distortion or disorganization of a person's mental capacity, affective response, and capacity to recognize reality, communicate, and relate to others to the degree of interfering with his capacity to cope with the ordinary demands of everyday life. In a condition or illness involving psychosis, delusions or hallucinations can be present. The content of the delusions or hallucinations have many depressive themes. In psychotic major depression there can be "mood-congruent" psychotic features, including, for example, delusions of guilt, delusions one deserves punishment (e.g. because of a personal inadequacy or moral transgression), nihilistic delusions (e.g. of world or personal destruction), somatic delusions (e.g. having cancer), or delusions of poverty. Hallucinations, when present in psychotic major depression are usually transient and not elaborate and may involve voices that berate the patient for shortcomings or sins. More rarely, the content of the delusions or hallucinations has no apparent relationship to depressive themes. In this situation these "mood-incongruent" psychotic features include, for example, grandiose delusions.

Psychosis can also include bipolar I disorder with psychotic features, brief psychotic disorder, delusional disorder, shared psychotic disorder, substance induced psychotic disorder and psychotic disorder not otherwise specified.

B. Formulations of Mifepristone

Formulations of the present invention include mifepristone in combination with pharmaceutical excipients. Mifepristone is commercially available from a variety of sources such as Eurolabs Ltd. (London, England). Mifepristone can also be synthesized by one of skill in the art using known synthetic procedures.

The term "mifepristone" refers to a family of compositions also referred to as RU486, or RU38.486, or 17-beta-hydroxy-11-beta-(4-dimethyl-aminophenyl)-17-alpha-(1-propynyl)-estra-4,9-dien-3-one), or 11-beta-(4-dimethylaminophenyl)-17-beta-hydroxy-17-alpha-(1-propynyl)-estra-4,9-dien-3-one), or analogs thereof, which bind to the GR, typically with high affinity, and inhibit the biological effects initiated/mediated by the binding of any cortisol or cortisol analogue to a GR receptor. Chemical names for RU-486 vary; for example, RU486 has also been termed: 11B-[p-(Dimethylamino)phenyl]-17B-hydroxy-17-(1-propynyl)-estra-4,9-dien-3-one; 11B-(4-dimethyl-aminophenyl)-17B-hydroxy-17A-(prop-1-ynyl)-estra-4,9-dien-3-one; 17B-hydroxy-11B-(4-dimethylaminophenyl-1)-17A-(propynyl-1)-estra-4,9-diene-3-one; 17B-hydroxy-11 B-(4-dimethylaminophenyl-1)-17A-(propynyl-1)-E; (11B,17B)-11-[4-dimethylamino)-phenyl]-17-hydroxy-17-(1-propynyl)estra-4,9-dien-3-one; and 11B-[4-(N,N-dimethylamino)phenyl]-17A-(prop-1-ynyl)-D-4,9-estradiene-17B-ol-3-one. Salts, hydrates and prodrug forms of mifepristone are also useful in the formulations of the present invention.

Formulations suitable for oral administration can consist of (a) liquid solutions, such as an effective amount of mifepristone suspended in diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, e.g., sucrose, as well as pastilles comprising the active ingredient in an inert base, such as gelatin and glycerin or sucrose and acacia emulsions, gels, and the like containing, in addition to the active ingredient, carriers known in the art.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form. The composition can, if desired, also contain other compatible therapeutic agents. Preferred pharmaceutical preparations can deliver the compounds of the invention in a sustained release formulation.

C. Administration of Mifepristone

The formulations of the present invention provide serum levels of mifepristone of at least 1300 ng/mL. The mifepristone utilized in the pharmaceutical method of the invention is administered at the initial dosage of about 0.001 mg/kg to about 1000 mg/kg daily. A daily dose range of about 0.01 mg/kg to about 500 mg/kg, or about 0.1 mg/kg to about 200 mg/kg, or about 1 mg/kg to about 100 mg/kg, or about 10 mg/kg to about 50 mg/kg, can be used. The dosages, however, may be varied depending upon the requirements of the patient and the condition being treated. The dose administered to a patient, in the context of the present invention, should be sufficient to effect a beneficial therapeutic response in the patient over time. The size of the dose also will be determined by the existence, nature, and extent of any adverse side-effects that accompany the administration of a particular compound in a particular patient. Determination of the proper dosage for a particular situation is within the skill of the practitioner.

Generally, treatment is initiated with six daily doses, with the blood levels tested on the day of the seventh daily dose in order to determine whether the dose used is providing a mifepristone blood level of at least 1300 ng/mL. The testing is also performed to ensure the blood levels are below those afforded by an LD50 dose of about 1000 mg/kg. If the mifepristone blood level is lower than 1300 ng/mL. Additional testing of mifepristone blood levels can be necessary in order to confirm a mifepristone blood level of at least 1300 ng/mL or to adjust the mifepristone daily dose higher. For convenience, the total daily dosage may be divided and administered in portions during the day, if desired. In addition, the interval from initiation of treatment and testing for mifepristone blood levels can be as short as 1 daily dose, or up to 28 daily doses and longer.

Mifepristone can be administered for any period of time, such as 7 daily doses over a period of seven days. Mifepristone can also be administered using more daily doses over a longer period of time, such as via 28 daily doses over a period of 28 days. Longer times for administration of mifepristone are also within the scope of the present invention.

D. Assay for Testing Mifepristone Levels

Mifepristone levels can be determined by any method known in the art. Methods for detecting mifepristone levels include, but are not limited to, radio-immuno assay and mass spectrometry (MALDI, SELDI, LS/MS, LS/MS/MS, among others). Liquid chromatography mass spectrometry (LC/MS or LC-MS) separates compounds chromatographically before they are introduced to the ion source and mass spectrometer. It differs from GC/MS in that the mobile phase is liquid, usually a combination of water and organic solvents, instead of gas. Most commonly, an electrospray ionization source is used in LC/MS.

Tandem mass spectrometry (MS/MS) involves multiple steps of mass selection or analysis, usually separated by some form of fragmentation. A tandem mass spectrometer is one capable of multiple rounds of mass spectrometry. For example, one mass analyzer can isolate one peptide from many entering a mass spectrometer. A second mass analyzer then stabilizes the peptide ions while they collide with a gas, causing them to fragment by collision-induced dissociation (CID). A third mass analyzer then catalogs the fragments produced from the peptides. Tandem MS can also be done in a single mass analyzer over time as in a quadrupole ion trap. There are various methods for fragmenting molecules for tandem MS, including collision-induced dissociation (CID), electron capture dissociation (ECD), electron transfer dissociation (ETD), infrared multiphoton dissociation (IRMPD) and blackbody infrared radiative dissociation (BIRD). One of skill in the art will appreciate that other assays for testing mifepristone levels are known to one of skill in the art.

In some embodiments, the assay can be performed as follows. Blood is collected from a patient in a vacutainer containing sodium heparin. The blood is centrifuged and the resulting plasma frozen at an appropriate temperature until assay. In some embodiments, the temperature is about −70° C. In other embodiments, other blood components can be collected and stored. Prior to analysis, the plasma is thawed and a fraction of the plasma is mixed with an internal standard in a solvent such as acetonitrile, to obtain a fixed concentration of the standard. In some embodiments, the internal standard can be mifepristone-$d_4$. The concentration of the internal standard is selected in order to be greater than the expected concentration of mifepristone in the plasma. For example, the internal standard can have a concentration of 2000 ng/mL. One of skill in the art will appreciate that other internal standards, and other concentrations, are useful in the present invention.

Base is then added to the sample solution. The base can be any amine or ammonium base, such as ammonium hydroxide. One of skill in the art will appreciate that other bases are useful in the present invention.

Solvent is then added to the solution and the mifepristone (along with the internal standard) are extracted from the plasma. Solvents useful for the extraction of mifepristone include, but are not limited to, hexanes, pentanes, ethers (such as diethylether, tetrahydrofuran and methyl-t-butyl ether (MTBE)), ethyl acetate, chloroform and methylene chloride. One of skill in the art will appreciate that other solvents are useful in the present invention.

Following separation and concentration of the organic layer, the sample is reconstituted in a solvent mixture comprising water, acetonitrile and formic acid. The ratio of the solvent components can vary. In some embodiments, the solvent mixture is water:acetonitrile:formic acid (75:25:0.1, v/v/v). One of skill in the art will appreciate that other solvent mixtures are useful in the present invention.

The sample can then be analyzed by reverse-phase high pressure liquid chromatography (HPLC). In some embodiments, the reverse-phase HPLC is performed using a water:acetonitrile:formic acid (60:40:0.1) mobile phase (isocratic) at a flow rate of 0.3 mL/min. One of skill in the art will appreciate that other mobile phases and flow rates are useful in the present invention.

The reverse-phase HPLC column can be a phenyl column maintained at 50° C. Mifepristone elutes at 4.2 minutes. Following elution, the mobile phase can be nebulized using heated nitrogen in a Z-spray source/interface and the ionized compounds detected using a tandem quadrupole mass spectrometer. Mifepristone (molecular weight of 430 g/mol) can be detected at m/z 372.30. The internal standard mifepristone-$d_4$ can be detected at m/z 376.30. The ratio of the mifepristone peak height to the peak height for the internal standard can then be calculated.

The plasma concentration of mifepristone is then calculated by comparing the experimental ratio to a standard curve of mifepristone:mifepristone-$d_4$ peak height ratio v. mifepristone concentration. The standard curve is generated by first measuring the mifepristone:mifepristone-$d_4$ peak height ratios for mifepristone samples at 10, 20, 50, 100, 200, 500, 1000 and 2000 ng/mL where the mifepristone-$d_4$ internal standard has a concentration of 2000 ng/mL. The mifepristone:mifepristone-$d_4$ peak height ratios of these known solutions are then fit to a power equation (Mass Lynx by Micromass, Beverly, Mass.), against which future samples with unknown concentrations of mifepristone are compared.

The plasma levels of mifepristone derivatives such as RU42633, RU42698 and RU42848, among others, can also be determined using the assay described above.

E. Kits for Treating Mental Disorders with Mifepristone

The present invention provides kits. The kits of the present invention comprise seven daily doses and a plasma sampling collection device. The kits of the present invention can also comprise any other component necessary for a kit, such as a container.

Patient plasma can be collected by any known plasma collection device. Some plasma collection devices useful in the present invention include, but are not limited to, vacutainers. The plasma collection devices of the present invention can optionally comprise additives in the device, such as anticoagulants (EDTA, sodium citrate, heparin, oxalate), a gel with intermediate density between blood cells and blood plasma, particles causing the blood to clot, a gel to separate blood cells from serum, thrombin and fluoride, among others.

The kits can also contain additional vessels used for further analysis of the plasma. For example, when the plasma is centrifuged, the centrifuged plasma can be transferred to a vessel, such as a cryostat tube. One of skill in the art will appreciate that other vessels and containers are useful in the present invention.

IV. Examples

Example 1

Determination of Mifepristone Plasma Level

This example provides a procedure for determining the plasma level of mifepristone in a patient.

Three (3) mL of blood was collected from a patient in a vacutainer containing sodium heparin. The blood was centrifuged and the resulting plasma frozen at −70 to −80° C. until assay. For analysis, the plasma samples were warmed and prepared as follows:
1. Using a pipette, 50.0 µL of the sample was aliquoted into a 16×100-mm glass test tube. When a partial volume aliquot was needed, the aliquot was added to the tube and diluted to full volume with blank human plasma.

2. 20.0 μL of the internal standard, mifepristone-$d_4$ (5.00 μg/mL in acetonitrile), was added to the tube, resulting in 2000.0 ng/mL mifepristone-$d_4$ in plasma.
3. The tube was vortexed for approximately 1 minute.
4. 50.0 μL of 6% ammonium hydroxide was added to the tube.
5. The tube was vortexed for approximately 1 minute.
6. 2.00 mL of MTBE was added to the tube.
7. 2.00 mL of hexane was added to the tube.
8. The tube was vortexed for at least 15 minutes.
9. The tube was centrifuged for at least 10 minutes at 2500 RPM (575×g).
10. The aqueous layer was frozen in a freezer set to maintain −70° C.
11. The upper organic layer was poured into a 13×100-mm polypropylene tube.
12. The organic layer was evaporated in a Turbovap set to 40° C.
13. 200.0 μL of a solution of water:acetonitrile:formic acid (75:25:0.1, v/v/v) was added to the tube.
14. The tube was vortexed for approximately 1 minute.
15. The tube was sonicated for approximately 1 minute.
16. The tube was vortexed for approximately 1 minute.
17. The sample was transferred to a labeled injection vial or well plate.
18. The vial or plate was capped and checked for air bubbles.

The sample was then analyzed by reverse-phase high pressure liquid chromatography using a water:acetonitrile:formic acid (60:40:0.1) mobile phase (isocratic) at a flow rate of 0.3 mL/min. The column was a phenyl column maintained at 50° C. Mifepristone elutes at 4.2 minutes. Following elution, the mobile phase was nebulized using heated nitrogen in a Z-spray source/interface and the ionized compounds detected using a tandem quadrupole mass spectrometer. Mifepristone (molecular weight of 430 g/mol) was detected at m/z 372.30. The internal standard mifepristone-$d_4$ was detected at m/z 376.30. The ratio of the mifepristone peak height to the mifepristone-$d_4$ peak height was calculated.

The plasma concentration of mifepristone was then calculated by comparing the experimental ratio to a standard curve of mifepristone:mifepristone-$d_4$ peak height ratio v. mifepristone concentration. The standard curve was generated by first measuring the mifepristone:mifepristone-$d_4$ peak height ratios for mifepristone samples at 10, 20, 50, 100, 200, 500, 1000 and 2000 ng/mL where the mifepristone-$d_4$ internal standard has a concentration of 2000 ng/mL. The mifepristone:mifepristone-$d_4$ peak height ratios of these known solutions were then fit to a power equation (Mass Lynx by Micromass, Beverly, Mass.), and the sample with unknown concentrations of mifepristone was compared.

Example 2

Phase III Trial with three dose levels of CORLUX™

This example provides a randomized, double-blind, placebo-controlled, parallel group study of the safety and efficacy of three dose levels of CORLUX™ (Mifepristone) plus an antidepressant vs. placebo plus an antidepressant in the treatment of psychotic symptoms in patients with major depressive disorder with psychotic features (PMD).

The study was a Phase III trial performed using several investigators at several different sites. The objectives were to demonstrate the efficacy and safety of three dose levels of CORLUX (mifepristone) combined with an antidepressant compared to placebo combined with an antidepressant in the treatment of psychotic symptoms in patients with Major Depressive Disorder with Psychotic Features (PMD).

The number of patients was less than 440. Patients eligible for randomization were male or nonpregnant female outpatients, and inpatients, if clinically required, with a diagnosis of Major Depressive Disorder with Psychotic Features (DSM-IV 296.24 or 296.34), and a BPRS Positive Symptom subscale score of at least 12, a BPRS total score of at least 38, and a HAMD-24 score of at least 20.

CORLUX was used as the test drug at 300 (1×300 mg tablet), 600 (2×300 mg tablet), and 1200 mg (4×300 mg tablet) once a day by mouth for the initial 7 days. Appropriate numbers of active and placebo tablets will be given to all dose groups so that each patient takes a total of 4 tablets at each daily dose. The reference drug was a placebo (1, 2, or 4 tablets matching CORLUX 300 mg tablets) once a day by mouth for the initial 7 days.

Up to 440 patients were randomly assigned to receive CORLUX 300, 600, or 1200 mg/day or placebo (in a 1:1:1:1 ratio) each day for 7 days. An antidepressant selected from a prescribed list was started simultaneously with the study drug, and continued to the end of the trial. BPRS and HAM-D assessments were performed at Screen and on Days 0, 7, 14, 28, 42, and 56, and at early termination when it occurred. Safety visits occurred at Days 21 and 35. The patients who are seen as outpatients made daily visits to the clinic setting to receive study medications for the first 7 days. If clinically necessary, a patient was treated as an inpatient.

In addition to the selected antidepressant, continuing benzodiazepines was allowed up to specified dose levels, but antipsychotics, mood stabilizers and additional antidepressants were not allowed during the entire study. If the patient was at imminent risk to him/herself and/or others and therefore could not be adequately treated within the study (e.g., required ECT, new or re-hospitalization for PMD, antipsychotics or mood stabilizers, or a second antidepressant), the patient underwent an early termination visit on the day that rescue therapy was started and completed final efficacy evaluations. If early termination occurred prior to day 35, the patient returned for a safety follow up visit at day 35.

The primary efficacy endpoint was the proportion of patients with at least a 50% reduction from baseline of the BPRS Positive Symptom Subscale (PSS) scores at Days 7 and 56. The secondary endpoints were: (1) the proportion of responders at days 7 and 28; and (2) the mean change from baseline to day 56 in the HAM-D-24 total score.

Adverse events, laboratory assessments including electrocardiograms, and physical examination were used to assess safety.

The criteria for assessing study efficacy objective was the proportion of patients with a reduction of at least 50% from baseline in BPRS Positive Symptom Subscale scores at Days 7 and 56.

Example 3

Phase III Trial for Study of the Efficacy and Safety of Corlux™

This example provides an international, double-blind, placebo-controlled study of the efficacy and safety of CORLUX™ (Mifepristone) vs. placebo in the treatment of psychotic symptoms in patients with Psychotic Major Depression (PMD).

The study was a Phase III trial performed using several investigators at several different international sites. The objective of the trial was to demonstrate the efficacy and safety of CORLUX (mifepristone) combined with an antidepressant compared to placebo combined with an antidepressant in the treatment of psychotic symptoms in patients with Major Depressive Disorder with Psychotic Features (PMD).

The number of patients was 220 evaluable subjects. Patients eligible for randomization were male or non-pregnant female outpatients, or inpatients, if necessary for patient well-being, with a diagnosis of Major Depressive Disorder with Psychotic Features (ICD-10 F32.3 or F33.3 or DSM-IV 296.24 or 296.34). At the screening and baseline visits, patients demonstrated the following severity of illness: BPRS Positive Symptom Subscale (PSS) score≥12; BPRS total score≥38, and HAMD-24 total score≥20.

CORLUX was administered in a 600 mg dose once a day by mouth for the initial 7 days (administered as two 300 mg tablets). Reference drug, dose, dosage regimen, route of administration: Matching placebo was administered once a day by mouth for the initial 7 days.

Up to 280 patients were randomly assigned (1:1 ratio) to receive either CORLUX 600 mg/day or placebo daily for 7 days. After the 7-day dosing period, patients were evaluated at Days 14, 21, 28, 35, 42 and 56. An antidepressant was administered simultaneously with study drug, and continued to the end of the trial (Day 56). BPRS and HAMD-24 assessments were performed at Screen and on Days 0, 7, 14, 28, 42 and 56, or at early termination. A safety visit occurred on Days 21 and 35, and at study termination on Day 56. Subjects treated on an outpatient basis made daily visits to the clinic to receive study medication for the first 7 days. Subjects were treated on an inpatient basis for as long as deemed clinically necessary by the investigator.

In addition to the selected antidepressant, concomitant benzodiazepine treatment was allowed up to specified dose levels. Antipsychotics, mood stabilizers and a second antidepressant were prohibited during the entire study. If the patient was at imminent risk to him/herself and/or others and therefore could not be adequately treated within the study (i.e., required ECT, new or re-hospitalization for PMD, antipsychotics or mood stabilizers, or a second antidepressant), the patient underwent an early termination visit on the day that rescue therapy was started, and completed procedures listed for the day 56 termination visit, including final efficacy evaluations. If early termination occurred prior to day 35, the patient returned for a safety follow-up visit at regularly scheduled day 35.

The Primary efficacy endpoint was determined by the proportion of patients with ≥50% reduction from baseline on the BPRS-PSS at Days 7 and 28. Key secondary efficacy endpoints include (1) the proportion of patients with ≥50% reduction from baseline on the BPRS-PSS at Days 7 and 56; and (2) change from baseline on the HAMD-24 at Day 56. Adverse events, laboratory assessments including electrocardiograms, and physical examination were used to assess safety.

Example 4

Treatment of Male Patient with PMD

A 50 year-old male, weighing 175 pounds, presents to physician with psychotic major depression (PMD). The physician prescribes 300 mg of mifepristone for seven daily doses over a period of seven days. One week later on the day of the seventh daily dose, three (3) mL of blood are collected from the patient and analyzed as described above in the specification. The dose of mifepristone is then adjusted, if necessary, to achieve mifepristone blood levels of greater than 1300 ng/mL. The mifepristone dose can be adjusted a single time to achieve mifepristone blood levels of greater than 1300 ng/mL. Alternatively, several adjustments to the mifepristone dose can be necessary to safely achieve mifepristone blood levels of greater than 1300 ng/mL.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference.

What is claimed is:

1. A method for optimizing levels of mifepristone in a patient suffering from a mental disorder amenable to treatment by mifepristone, the method comprising:
    treating the patient with seven or more daily doses of mifepristone over a period of seven or more days;
    testing the serum levels of the patient to determine whether the blood levels of mifepristone are greater than 1300 ng/mL; and
    adjusting the daily dose of the patient to achieve mifepristone blood levels greater than 1300 ng/mL.

2. The method of claim 1, wherein the mental disorder is a member selected from the group consisting of a stress disorder, delirium, mild cognitive impairment (MCI), dementia, psychosis and psychotic major depression.

3. The method of claim 2, wherein the stress disorder is a member selected from the group consisting of Acute Stress Disorder, Post-Traumatic Stress Disorder and Brief Psychotic Disorder with Marked Stressor(s).

4. The method of claim 1, wherein each of the seven or more daily doses of mifepristone are administered orally.

5. The method of claim 1, wherein the patient is treated with 28 or more daily doses over a period of 28 or more days.

6. The method of claim 1, wherein the testing is performed by a plasma sampling collection device suitable for detecting mifepristone serum levels.

7. The method of claim 1, wherein the adjusting step comprises increasing the daily dose of the patient to achieve mifepristone blood levels greater than 1300 ng/mL.

* * * * *

UNITED STATES PATENT AND TRADEMARK OFFICE
CERTIFICATE OF CORRECTION

| | | |
|---|---|---|
| PATENT NO. | : 8,598,149 B2 | Page 1 of 1 |
| APPLICATION NO. | : 12/199114 | |
| DATED | : December 3, 2013 | |
| INVENTOR(S) | : Belanoff et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 990 days.

Signed and Sealed this
Thirtieth Day of December, 2014

Michelle K. Lee
*Deputy Director of the United States Patent and Trademark Office*